United States Patent [19]

Berrocal et al.

[11] Patent Number: 5,427,769
[45] Date of Patent: Jun. 27, 1995

[54] PREVENTION OF DENTAL CARIES

[75] Inventors: Rafael Berrocal, St-Legier; Bernhard Guggenheim, Zurich; Jean-Richard Nesser, Savigny, all of Switzerland

[73] Assignee: Nestec S.A., Vevey, Switzerland

[21] Appl. No.: 162,855

[22] Filed: Dec. 6, 1993

[30] Foreign Application Priority Data

Dec. 28, 1992 [CH] Switzerland .......................... 3971/92

[51] Int. Cl.$^6$ .......................... A61K 7/16; A61K 7/22; A61K 35/20
[52] U.S. Cl. .......................... 424/54; 424/49; 424/535; 426/580; 426/582; 530/832; 530/833
[58] Field of Search .................. 424/54, 535; 426/580, 426/582; 530/832, 833

[56] References Cited

U.S. PATENT DOCUMENTS

| | | | |
|---|---|---|---|
| 4,244,971 | 1/1981 | Wargel et al. | 426/35 |
| 4,540,594 | 9/1985 | Schanze | 426/74 |
| 4,992,420 | 2/1991 | Neeser | 514/8 |
| 4,994,441 | 2/1991 | Nesser . | |
| 5,015,628 | 5/1991 | Reynolds . | |
| 5,143,741 | 9/1992 | Podolski et al. | 426/565 |

FOREIGN PATENT DOCUMENTS

| | | |
|---|---|---|
| 2672494 | 8/1992 | France . |
| 2212380 | 7/1989 | United Kingdom . |
| WO8203008 | 9/1982 | WIPO . |

OTHER PUBLICATIONS

Madinier, Abstract, International Patent Application Publication No. WO 92/14475 (Aug. 1992).
Sperling, et al. Effect of Long Time Feeding of Whole Milk Diets to White Rats. Journal of Nutrition, vol. 55, 1955 pp. 399–414.
Reynolds, et al; Effect of Milk on Caries Incidence and Bacterial Composition of Dental Plaque In the Rat. Archives of Oral Biology, vol. 26, 1981, pp. 445–451.
White, Milk, Milk Products, and Dental Health. Journal of Dairy Science, vol. 70, No. 2, Jun. 1987 pp. 392–396.
Fauquant, et al., Microfiltration of Milk Using a Mineral Membrane. Food, Science and Technology Abstracts No. 88-10-P0221. Aug. 1988.

*Primary Examiner*—Shep K. Roses
*Attorney, Agent, or Firm*—Vogt & O'Donnell

[57] ABSTRACT

Dental caries are prevented by contacting teeth with an edible composition containing micellar casein which has been isolated from an animal milk and which is incorporated in the composition in an amount sufficient to inhibit oral colonization by *Streptococcus sobrinus*.

4 Claims, No Drawings

PREVENTION OF DENTAL CARIES

BACKGROUND OF THE INVENTION

This invention relates to an anti-cariogenic.

Certain casein derivatives are known for their anti-cariogenic properties.

Thus, U.S. Pat. No. 5,015,628 (University of Melbourne) describes an anti-cariogenic composition containing in particular phosphopeptides obtained, for example, by trypsic hydrolysis of alpha or beta casein as the active agent.

U.S. Pat. No. 4,994,441 (Nestec S. A.) describes an anti-plaque and anti-caries composition in which the active agent is selected from kappa-caseinoglycopeptides and their desialylated derivatives.

On the same subject, French Patent Application Publication No. 2 672 494 (Dr. Madinier) describes prophylactic ferments which assist in the prevention of dental caries. These ferments may be used either on their own or in combination with ferments used for the production of yoghurt for example.

DESCRIPTION OF THE INVENTION

The problem addressed by the present invention was to provide an anti-cariogenic food composition containing an active agent in substantially native form.

To this end, the anti-cariogenic food composition according to the invention contains an effective quantity of micellar casein.

It has in fact surprisingly been found that casein itself shows remarkable anti-cariogenic activity providing it is in its micellar form.

The present invention also relates to the use of a micellar casein in an effective quantity for the production of an anti-cariogenic food composition.

In the composition according to the invention or for the use according to the invention, the micellar casein may originate, for example, from an animal milk, such as cow's milk, goat's milk or ewe's milk.

This micellar casein may be obtained, for example, by microfiltration, ultrafiltration and/or diafiltration of the animal milk.

The micellar protein is preferably obtained by microfiltration of the animal milk through a mineral membrane having a porosity of, for example, approximately 0.1 to 0.2 $\mu$m.

In one preferred embodiment of the composition or the use according to the invention, constituents of the animal milk different from casein are added to or mixed with the micellar casein in a proportion similar to that encountered in an animal milk.

EXAMPLES

The following Examples are intended to illustrate the composition and the use according to the invention and to demonstrate the anti-cariogenic properties in question.

In the Examples, percentages and parts are by weight unless otherwise indicated.

Example 1, Comparison Examples i)–iii)

Four compositions are prepared, one of which corresponds to the invention while the other three are intended for comparison. Each composition contains 30% sucrose, 32% wheat flour, 5% brewer's yeast and 2% micronutriments (Gevral mixture), the remaining 30% consisting of:

Example 1: commercial skimmed cow's milk powder
Comparison Example i): caseinate-based substitute for skimmed cow's milk powder consisting of:

| | |
|---|---|
| Sodium caseinate | 41.9% |
| Lactose | 49.1% |
| $Ca_3(C_6H_5O_7)_2 \cdot 4H_2O$ | 2.3% |
| $CaCl_2$ | 1.8% |
| $MgCl_2 \cdot 6H_2O$ | 0.7% |
| $K_2HPO_4 \cdot 3H_2O$ | 4.2% |

Comparison Example ii): whey-based substitute for skimmed cow's milk powder consisting of:

| | |
|---|---|
| Whey protein concentrate (80% proteins) | 45.4% |
| Lactose | 45.3% |
| $Ca_3(C_6H_5O_7)_2 \cdot 4H_2O$ | 2.0% |
| $CaCl_2$ | 1.5% |
| $MgCl_2 \cdot 6H_2O$ | 0.6% |
| $K_2HPO_4 \cdot 3H_2O$ | 3.4% |
| $Na_2HPO_4$ | 1.6% |
| Histidine.HCl—$H_2O$ | 0.2% |

Comparison Example iii): soya protein substitute for skimmed cow's milk powder consisting of:

| | |
|---|---|
| Soya protein isolate (91% proteins) | 39.3% |
| Lactose | 49.3% |
| $Ca_3(C_6H_5O_7)_2 \cdot 4H_2O$ | 2.4% |
| $CaCl_2$ | 1.9% |
| $MgCl_2 \cdot 6H_2O$ | 0.5% |
| $K_2HPO_4 \cdot 3H_2O$ | 4.3% |
| $Na_2HPO_4$ | 1.9% |
| L-methionine | 0.3% |
| L-lysine.HCl | 0.1% |

Six litters of Osborne-Mendel rats each comprising four rats born on day 0 are used. On day 13, the rats and their mothers are transferred to stainless steel cages with grill bases where they are fed with granules of Nafag concentrate and tapwater as required until day 20. The rats are then randomly distributed into groups of 6. The rats of each group are fed with one of the four compositions described above and are given tapwater as required.

On days 21 and 22, each rat is given 100 $\mu$l of a concentrated suspension of *Streptococcus sobrinus* (OMZ-176) and *Actinomyces viscosus* (Ny-1) twice a day.

On day 40, the level of dental plaque, the number of dental caries (incipient fissures, advanced fissures and smooth surface caries) and the increase in weight are determined by routine procedures. The results are set out in Table I below.

In Table I, the scale of dental plaque is marked from 0 to 4, a mark of 0 being equivalent to no plaque and a mark of 4 being equivalent to maximal plaque. The number of incipient and advanced fissures is based on a maximum of 12, the number of smooth surface caries is based on a maximum of 20. The increase in weight is expressed in g.

TABLE I

| Ex.No. | Dental plaque | Incipient fissures | Advanced fissures | Smooth surface caries | Increase in weight |
|---|---|---|---|---|---|
| 1 | 2.8 | 7.1 | 2.7 | 6.2 | 105 |
| i) | 2.5 | 9.0 | 4.9 | 13.6 | 102 |

TABLE I-continued

| Ex.No. | Dental plaque | Incipient fissures | Advanced fissures | Smooth surface caries | Increase in weight |
|---|---|---|---|---|---|
| ii) | 2.0 | 7.8 | 3.9 | 12.3 | 96 |
| iii) | 2.3 | 9.5 | 6.1 | 12.3 | 102 |

It can be seen that the best diet is undoubtedly the diet where the rats are given the composition according to Example 1 containing casein from cow's milk in micellar form. All the compositions used for comparison, none of which contains micellar casein, cause more caries for a comparable increase in weight.

Examples 2 and 3, Comparison Examples iv) and v)

Four compositions are prepared, two of which correspond to the invention while the other two are intended for comparison. Each composition contains 30% sucrose, 32% wheat flour, 5% brewer's yeast and 2% micronutriments (Gevral mixture), the remaining 30% consisting of:

Example 2: commercial skimmed cow's milk powder
Example 3: fresh commercial cow's milk skimmed at 37 to 40° C. and spray dried below 70° C.
Comparison Example iv): commercial skimmed fresh cow's milk acidified to pH 5 by addition of 2N HCl, neutralized by addition of 2N KOH and then spray-dried
Comparison Example v): soya-based substitute for skimmed cow's milk powder having the same composition as that described in Comparison Example iii)

Six litters of Osborne-Mendel rats each comprising four rats born on day 0 are used. On day 13, the rats and their mothers are transferred to stainless steel cages with grill bases where they are fed with granules of Nafag concentrate and tapwater as required until day 20. The rats are then randomly distributed into groups of 6. The rats of each group are fed with one of the four compositions described above and are given tapwater as required.

On days 21 and 22, each rat is given 100 µl of a concentrated suspension of *Streptococcus sobrinus* (OMZ-176) and *Actinomyces viscosus* (Ny-1) twice a day.

On day 40, the microbiological condition of the rats is determined. To this end, samples are taken by oral smear, the samples are suspended in 5 ml RTF fluid and 50 µl aliquots are spotted onto two solid culture media, namely Columbia blood-containing agar plates containing 5% haemolyzed human blood and TYS agar plates containing 5% sucrose.

The blood-containing agar plates are used to determine the total number of cultivatable anaerobic bacteria, i.e. the total number of anaerobic colony forming units (cfu) and the number of colony forming units of *A. viscosus*. The TS agar plates are used to determine the total number of bacteria cultivatable on these plates and the number of colony forming units of *S. sobrinus*. The results are set out in Table II below.

TABLE II

| | Blood-containing agar cfu × 10⁶ | | TYS agar cfu × 10⁶ | |
|---|---|---|---|---|
| Ex.No. | Total | A.viscosus | Total | S.sobrinus |
| 2 | 78.0 | 45.8% | 63.4 | 15.0% |
| 3 | 55.0 | 39.6% | 40.8 | 11.1% |
| iv) | 62.0 | 18.5% | 44.6 | 45.9% |
| v) | 51.0 | 8.3% | 41.0 | 54.8% |

It can be seen from Table II that the diets where the rats are given the compositions according to Examples 2 and 3, which contain casein from cow's milk in micellar form, have a beneficial effect on the oral flora because the significantly reduce the proportion of *S. sobrinus* but, at the same time, increase the proportion of *A. viscosus* encountered there. The opposite phenomenon is observed with those diets where the rats are given the compositions according to Comparison Examples iv) and v), of which the first contains a casein where the micellar structure has been destroyed and of which the second does not contain any casein at all.

On day 40, the scale of dental plaque, the number of dental caries (incipient fissures, advanced fissures and smooth surface caries) and the increase in weight are determined by routine procedures. The results expressed similarly to those of Table I are set out in Table III below.

TABLE III

| Ex.No. | Dental plaque | Incipient fissures | Advanced fissures | Smooth surface caries | Increase in weight |
|---|---|---|---|---|---|
| 2 | 1.6 | 9.3 | 4.5 | 4.8 | 116 |
| 3 | 1.3 | 8.8 | 3.9 | 4.3 | 111 |
| iv) | 1.6 | 9.9 | 5.8 | 7.3 | 112 |
| v) | 1.7 | 10.9 | 8.4 | 9.6 | 106 |

The results set out in Table III show that the diet where the rats are given the composition of Example 3, which contains casein from a fresh cow's milk whose micellar structure has not been destroyed, is as good as or even better than the diet where the rats are given the composition of Example 2 which also contains casein from cow's milk in micellar form. By contrast, the composition according to Comparison Example iv), which contains casein from a fresh cow's milk whose micellar structure has been destroyed, and the composition according to Comparison Example v), which does not contain any casein at all, cause more caries for a comparable increase in weight.

Examples 4 and 5, Comparison Example vi)

Three compositions are prepared, two of which correspond to the invention while the third is intended for comparison. Each composition contains 40% sucrose, 22% wheat flour, 5% brewer's yeast and 2% micronutriments (Gevral mixture), the remaining 30% consisting of:

Example 4: commercial skimmed cow's milk powder
Example 5: skimmed milk powder substitute consisting of:

| Micellar casein | 44.4% |
|---|---|
| Lactose | 49.2% |
| Na$_3$(C$_6$H$_5$O$_7$)$_2$.2H$_2$O | 2.4% |
| KCl | 1.1% |
| MgCl$_2$.6H$_2$O | 0.6% |
| K$_2$HPO$_4$.3H$_2$O | 2.3% |

(the micellar casein was prepared by microfiltration of a fresh commercial skimmed cow's milk and spray drying)

Comparison Example vi): caseinate-based skimmed cow's milk powder substitute having the same composition as that described in Comparison Example i)

Six litters of Osborne-Mendel rats each comprising four rats born on day 0 are used. On day 13, the rats and their mothers are transferred to stainless steel cages with grill bases where they are fed with granules of Nafag concentrate and tapwater as required until day 20. The rats are then randomly distributed into groups of 6. The rats of each group are fed with one of the three compositions described above and are given tapwater as required.

On days 21 and 22, each rat is given 100 μl of a concentrated suspension of Streptococcus sobrinus (OMZ-176) and Actinomyces viscosus (Ny-1) twice a day.

On day 40, the microbiological condition of the rats is determined. To this end, dental plaque samples are prepared by grinding the first and second molars of the left upper jaw of 6 rats of each group. The procedure is then as described above in Examples 2, 3, iv) and v). The results are set out in Table IV below.

TABLE IV

| Ex.No. | Blood-containing agar cfu × $10^6$ | | TYS agar cfu × $10^6$ | |
|---|---|---|---|---|
| | Total | A. viscosus | Total | S. sobrinus |
| 4 | 4.3 | 31.8% | 5.1 | 59.4% |
| 5 | 3.9 | 29.2% | 5.3 | 60.1% |
| vi) | 5.7 | 12.0% | 4.9 | 84.1% |

It can be seen from Table IV, where the results confirm those set out in Table II, that the diets in which the rats are given the compositions of Examples 4 and 5, which contain casein from cow's milk in micellar form, have a beneficial effect on the oral flora because they significantly reduce the proportion of S. sobrinus but, at the same time, increase the proportion of A. viscosus encountered there. The opposite phenomenon is again observed with the diet in which the rats are given the composition of Comparison Example vi) which contains a casein whose micellar structure has been destroyed.

On day 40, the scale of dental plaque, the number of dental caries (incipient fissures, advanced fissures and smooth surface caries) and the increase in weight are determined by routine procedures. The results expressed similarly to those of Table I are set out in Table V below.

TABLE V

| Ex.No. | Dental plaque | Incipient fissures | Advanced fissures | Smooth surface caries | Increase in weight |
|---|---|---|---|---|---|
| 4 | 1.8 | 11.0 | 8.0 | 13.9 | 100 |
| 5 | 1.2 | 10.1 | 4.4 | 9.6 | 99 |
| vi) | 2.0 | 11.4 | 9.5 | 19.3 | 100 |

The results set out in Table V show that the composition of Example 5, which contains casein from fresh cow's milk whose micellar form has been retained by microfiltration, shows particularly clear anti-cariogenic properties if it is compared with the effects of the composition of Comparison Example vi) which contains a cow's milk casein whose micellar form has been destroyed. The results of Example 4 are also good compared with those of Example vi), taking into consideration the fact that the sucrose content of the composition of this group of Examples is 40% as opposed to 30% in the preceding groups of Examples.

Example 6

A composition for a baby food is prepared by mixing the following components in the following proportions:

| Micellar casein | 6.3% |
|---|---|
| Demineralized whey powder (12.5% proteins) | 68.6% |
| Milk fats | 20.6% |
| Corn oil | 4.4% |
| $K_2HPO_4$ | 0.1% |

(the micellar casein having been prepared by microfiltration of a fresh commercial skimmed cow's milk and spray drying).

Example 7

A composition for a baby food is prepared by mixing the following components in the following proportions:

| Micellar casein | 12.6% |
|---|---|
| Demineralized whey powder (12.5% proteins) | 22.9% |
| Lactose | 34.9% |
| Milk fats | 20.4% |
| Corn oil | 4.6% |
| Minerals, micronutriments and water | 4.6% |

(the micellar casein having been prepared by microfiltration of a fresh commercial skimmed cow's milk and spray drying).

Example 8

A composition for a milk-based beverage is prepared by mixing between 3 and 15 g micellar casein prepared by microfiltration of a fresh commercial skimmed cow's milk and spray drying and between 5 and 20 g lactose for a quantity of water of 70 to 90 g, the sum total of these components having to be 100 g.

Example 9

A composition for a powder-form coffee cream substitute is prepared by mixing the following components in the following proportions:

| Micellar casein | between 2 and 31% |
|---|---|
| Lactose | between 31 and 60% |
| Partly hydrogenated coconut oil | 33% |
| Minerals, flavourings and water | 5%, | the sum total of these components having to be 100%.

The micellar casein was prepared by microfiltration of a fresh commercial skimmed cow's milk and spray drying.

We claim:

1. A method for preventing dental caries comprising contacting teeth with an edible composition comprising micellar casein which has been isolated from an animal milk and which is incorporated into the composition in an amount sufficient to inhibit oral colonization by Streptococcus sobrinus.

2. A method according to claim 1 wherein the micellar casein has been isolated from animal milk by microfiltration.

3. A method according to claim 1 wherein the micellar casein has been isolated from animal milk by ultrafiltration.

4. A process according to claim 1 wherein the micellar casein has been isolated from animal milk by diafiltration.

* * * * *

UNITED STATES PATENT AND TRADEMARK OFFICE
CERTIFICATE OF CORRECTION

PATENT NO. : 5,427,769
DATED : June 27, 1995
INVENTOR(S) : Rafael BERROCAL, et al.

It is certified that error appears in the above-indentified patent and that said Letters Patent is hereby corrected as shown below:

On the title page, in item [75] Inventors (left column), change "Nesser to --Neeser".

Signed and Sealed this

Twelfth Day of September, 1995

Attest:

BRUCE LEHMAN

Attesting Officer

Commissioner of Patents and Trademarks